United States Patent
Patel et al.

(10) Patent No.: US 11,766,389 B2
(45) Date of Patent: Sep. 26, 2023

(54) MAKEUP COMPOSITION

(71) Applicant: L'OREAL, Paris (FR)

(72) Inventors: Sonal Patel, Iselin, NJ (US); Balanda Atis, Green Brook, NJ (US)

(73) Assignee: L'OREAL, Paris (FR)

( * ) Notice: Subject to any disclaimer, the term of this patent is extended or adjusted under 35 U.S.C. 154(b) by 19 days.

(21) Appl. No.: 17/084,042

(22) Filed: Oct. 29, 2020

(65) Prior Publication Data

US 2022/0133609 A1 May 5, 2022

(51) Int. Cl.
| | |
|---|---|
| *A61Q 1/02* | (2006.01) |
| *A61Q 19/00* | (2006.01) |
| *A61Q 1/00* | (2006.01) |
| *A61K 8/25* | (2006.01) |
| *A61K 8/06* | (2006.01) |
| *A61K 8/891* | (2006.01) |
| *A61K 8/29* | (2006.01) |
| *A61K 8/73* | (2006.01) |
| *A61K 8/19* | (2006.01) |
| *A61K 8/96* | (2006.01) |

(52) U.S. Cl.
CPC ............. *A61K 8/29* (2013.01); *A61K 8/06* (2013.01); *A61K 8/19* (2013.01); *A61K 8/25* (2013.01); *A61K 8/732* (2013.01); *A61K 8/891* (2013.01); *A61K 8/965* (2013.01); *A61Q 1/02* (2013.01)

(58) Field of Classification Search
CPC . A61Q 1/02; A61Q 19/00; A61Q 1/10; A61Q 1/06; A61Q 17/04; A61Q 1/08; A61Q 1/04; A61Q 19/08; A61Q 1/00; A61K 8/064; A61K 8/06; A61K 8/04; A61K 8/891; A61K 8/25; A61K 8/89; A61K 8/29; A61K 8/00; A61K 2800/43; A61K 9/0014; A61K 2800/10
See application file for complete search history.

(56) References Cited

U.S. PATENT DOCUMENTS

| | | | |
|---|---|---|---|
| 5,505,937 A | 4/1996 | Castrogiovanni et al. | |
| 5,911,974 A | 6/1999 | Brieva et al. | |
| 5,965,112 A | 10/1999 | Brieva et al. | |
| 5,985,298 A | 11/1999 | Brieva et al. | |
| 6,074,654 A | 6/2000 | Drechsler et al. | |
| 6,426,079 B1* | 7/2002 | Bara ..................... | A61Q 19/00 424/401 |
| 6,509,024 B2 | 1/2003 | Lorant | |
| 6,780,422 B2 | 8/2004 | Brieva et al. | |
| 6,908,621 B2 | 6/2005 | Jose et al. | |
| 7,470,725 B2 | 12/2008 | Schwertfeger et al. | |
| 8,586,013 B2 | 11/2013 | Bradshaw et al. | |
| 2003/0235552 A1* | 12/2003 | Yu ......................... | A61Q 19/00 424/70.122 |
| 2004/0265346 A1 | 12/2004 | Verloo et al. | |
| 2005/0031560 A9* | 2/2005 | Simonnet ............... | A61K 8/604 424/63 |
| 2005/0074420 A1* | 4/2005 | Bourdel ................. | A61K 8/585 424/70.12 |
| 2006/0292096 A1 | 12/2006 | Yu | |
| 2007/0093619 A1 | 4/2007 | Bui et al. | |
| 2012/0301415 A1 | 11/2012 | Bui et al. | |
| 2012/0301416 A1* | 11/2012 | Marotta .................. | A61Q 1/10 424/70.7 |
| 2012/0328542 A1* | 12/2012 | Samain .................. | A61K 8/33 424/59 |
| 2014/0370062 A1* | 12/2014 | Fageon ................. | A61K 8/4966 424/401 |
| 2020/0289385 A1* | 9/2020 | Pagis ..................... | A61Q 1/00 |

FOREIGN PATENT DOCUMENTS

| | | |
|---|---|---|
| FR | 3067595 A1 | 12/2018 |
| WO | 2013/117551 A1 | 8/2013 |
| WO | 2018228783 A1 | 12/2018 |

OTHER PUBLICATIONS

French Search Report and Written Opinion dated Sep. 28, 2021 in French Patent No. 2012994, pp. 1-2.
Oil Block Base SPF 30 PA++, Mintel GNPD, Record ID 7306831, p. 1-4, Published on Mar. 2, 2020.
Hydrating Foundation Natural Healthy Look, Mintel GNPD, Record ID 7525745, p. 1-6, Published on Apr. 7, 2020.

* cited by examiner

*Primary Examiner* — Tracy Liu
(74) *Attorney, Agent, or Firm* — WOMBLE BOND DICKINSON (US) LLP

(57) ABSTRACT

A make-up emulsion composition includes an aqueous internal phase emulsified in an external fatty phase. The fatty phase includes at least one silicone oil, silicone resin, silica aerogel, spherical silica, clay, starch, pigment, and emulsifier. Methods of use are also provided.

14 Claims, No Drawings

MAKEUP COMPOSITION

TECHNICAL FIELD

The present disclosure relates to compositions for making up or cosmetically enhancing keratinous substrates, as well as methods of using the compositions.

BACKGROUND

Color cosmetic products have been long used to improve the appearance of keratinous substrates and, in particular, skin. While long-wear or extended wear makeup formulas are in use, these products still have limitations. It is difficult to formulate products that are phase stable, provide good color coverage, have appealing texture and comfort, as well as resistance to sweat and transfer from the skin and are able to hide the appearance of skin pores. Compositions and methods of the present invention overcome one or more of the above-mentioned drawbacks.

SUMMARY

According to one aspect of the invention, a make-up emulsion composition includes an aqueous internal phase emulsified in an external fatty phase. The fatty phase includes at least one silicone oil, silicone resin, silica aerogel, spherical silica, clay, starch, pigment, and emulsifier.

According to certain embodiments the emulsion composition may meet one or more of the following requirements: each of the clay, the starch, the spherical silica and silica silylate are present in concentrations by weight less than about 6.5%, such as from about 0.25% to about 6.5%, such as from about 0.25% to about 5%; and/or the sum of the concentrations by weight of the clay, the starch, the spherical silica and the silica silylate is from about 3% to about 10%, such as from about 3% to about 8%.

According to another aspect of the invention, a method of making up the skin includes applying a make-up emulsion composition to the skin. The composition includes an aqueous internal phase emulsified in an external fatty phase. The fatty phase includes at least one silicone oil, silicone resin, silica aerogel, spherical silica, clay, starch, pigment, and emulsifier.

DETAILED DESCRIPTION

All percentages of ingredients herein are listed on an actives basis unless specifically stated otherwise. Further, all percentages of ingredients are in percent by weight unless specifically stated otherwise. Furthermore, all weights are based on the weight of the composition as a whole unless otherwise specifically stated.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 15%, such as within 10%, of the indicated number. For example, about 10% means from 8.5% to 11.5%, such as between 9% and 11%.

"Oil" as used herein, means nonaqueous compounds having a melting point of less than about 25° C. and at atmospheric pressure ($1.013 \times 10^5$ Pa). Oils are generally immiscible with water wherein "immiscible" is intended to mean that the mixing of the same amount of water and oil, after mixing (for example Rayneri 550 rpm; 10 minutes), does not result in a stable solution including just one phase, under normal temperature and pressure conditions. Oils may be silicone-based, hydrocarbon based, or a combination thereof.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated using test methods described herein.

"Substituted" as used herein, means comprising at least one substituent. Non-limiting examples of substituents include atoms, such as oxygen atoms and nitrogen atoms, as well as functional groups, such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphategroups, siloxane groups, and polysiloxane groups. The substituent(s) may be further substituted.

"Substantially free" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. In certain embodiments, substantially free means less than about 2% of the identified ingredient, such as less than about 1%, such as less than about 0.5%, such as less than about 0.1% of the ingredient. The term "anhydrous" means substantially free of water.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

All concentrations in this specification are by weight unless otherwise specifically stated differently.

"Keratinous materials" includes materials containing keratin such as hair, skin, eyebrows, lips and nails. According to certain notable embodiments, the keratinous substrate is skin, such as skin of the face including around the cheeks, forehead, eyes, lips, or skin on other parts of the body.

"Volatile", as used herein, means having a flash point of less than about 100° C.

"Non-volatile", as used herein, means having a flash point of greater than about 100° C.

"Actives basis" as used herein means considering only the particular component of ingredient (e.g., in a composition) and ignoring other chemically unrelated components that may be also be present in the same raw material source of that particular component.

"Polymer" as used herein refers to a compound having molecules that comprise repeat units. In certain embodiments, polymer useful for embodiments described herein have a repeat unit comprising carbon and hydrogen, such as repeat units comprising carbon, hydrogen and optionally oxygen or nitrogen.

The compositions and methods of the present invention can comprise, consist of, or consist essentially of the essential elements and limitations of the invention described herein, as well as any additional or optional ingredients, components, or limitations described herein or otherwise useful.

The present disclosure relates to methods treating keratinous substrates using makeup setting compositions. The makeup setting compositions are in the form of an emulsion having a external fatty phase. By "external fatty phase" it is meant that the external phase comprises one or more fatty compounds such as silicone oils or waxes, hydrocarbon oils or waxes, and the like. Compositions of the present invention may be in the form of a two-phase system, what is commonly called water-in-oil (W/O) or water-in-silicone (W/S), or a three phase system, e.g., O/W/O S/W/S. In certain notable embodiments, the external fatty phase includes a percentage of silicone oils and/or silicone waxes that is greater than a percentage of hydrocarbon oils and/or hydrocarbon waxes in the external fatty phase.

Makeup Composition

Makeup compositions of the present invention include an external fatty phase that includes at least one silicone compound. The compositions further include a silicone resin, a silica aerogel, a spherical silica, a clay, starch, water, pigment, and emulsifier. These constituents are described below.

Silicone Compound

Compositions of the present invention include one or more silicone compounds that help serve as a vehicle for the formulation. Suitable silicone compounds include those that are liquid at room temperature. Examples of such silicone compounds are non-volatile silicone oils. The terms "oil" and "non-volatile" are as described above. According to certain embodiments, the non-volatile oil has a vapor pressure at 25° C. and atmospheric pressure that is non-zero and is less than 0.02 mmHg (2.66 Pa) and better still less than $10^{-3}$ mmHg (0.13 Pa).

According to a particular embodiment of the present invention, the non-volatile silicone oil is a low viscosity oil. "Low viscosity" means an oil having a viscosity less than about 100 cSt, particularly less than 50 cSt at 25° C.

In particular, the non-volatile silicone oils that may be used in the invention preferably have a viscosity at 25° C. between 1 cSt and 20 cSt. The viscosity of these silicone oils may be measured according to standard ASTM D-445.

According to certain embodiments, the non-volatile silicone oil is a non-phenylated silicone oil. The expression "non phenylated silicone oil" or "non phenylated silicone oil" means a silicon oil having no phenyl substituent.

According to one embodiment, a composition according to the invention contains at least one non-phenylated linear silicone oil. Representative examples of these non-volatile non phenylated silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Non-limiting examples of suitable non-volatile silicone oils include polymethylsiloxanes (PDMS) with a linear or cyclic silicone chain, which are liquid at room temperature, especially cyclopolydimethylsiloxanes (cyclomethicones) such as cyclohexasiloxane; polydimethylsiloxanes (CTFA designation "dimethicones") including alkyl or alkoxy groups, which are pendent or at the end of a silicone chain, these groups containing from 2 to 24 carbon atoms; polydiethyl siloxanes; and dimethicone fluids having viscosity from about 300 cPs at 25° C. to about 1500 cPs at 25° C. Particularly useful dimethicone fluids have viscosity from about 350 cPs at 25° C. to about 1000 cPs at 25° C. In certain embodiments, the silicone oil is phenylated.

"Dimethicone" (INCI Name) corresponds to polydimethylsiloxane (chemical name).

Specific examples of suitable for this invention high viscosity silicone oils include, but are not limited to, Xiameter® silicone fluids from Dow Corning. One notable example is XIAMETER PMX-200 SILICONE FLUID 2 CST.

The at least one silicone oil, if present, is preferably present in the compositions of the present invention in an amount ranging from about 5%, 10%, 15% or 20% to about 20%, 25%, 30% or 40% by weight.

Aside from the silicone oil described above, additional silicone compounds may also be used in combination with the above silicone oils. The additional silicone compounds may be liquid, pasty or solid at room temperature. Examples include polyalkylmethylsiloxanes such as cetyldimethicone sold under the commercial reference ABIL WAX 9801 from Evonik Goldschmidt, or polyalkylmethylsiloxane optionally substituted with a fluorinated group, such as polymemyltrifluoropropyldimethylsiloxanes. The additional silicone compounds may be modified with various substituents, such as those that may render the silicone compound such that it does not meet the definition of silicone oil. For example, certain PDMSs may include alkyl or alkoxy groups, which are pendent and/or at the end of the silicone chain, these groups each containing from 2 to 24 carbon atoms, such as cetyldimethicone sold under the commercial reference ABIL WAX 9801 from Evonik Goldschmidt, The PDMS may include aliphatic and/or aromatic groups, or functional groups such as hydroxyl, thiol and/or amine groups.

Silicone Resin

The makeup compositions of the present invention include at least one silicone resin. Examples of suitable silicone resins include those described, for example, in U.S. Pat. Nos. 5,505,937, 5,911,974, 5,965,112, 5,985,298, 6,074,654, 6,780,422, 6,908,621, the disclosures of which are hereby incorporated by reference in their entirety.

According to preferred embodiments, the long-wear lip compositions contain siloxysilicate resins. One non-limiting example of a siloxysilicate in accordance with the present invention is trimethylsiloxysilicate, which may be represented by the following formula:

[(CH$_3$)$_3$SiO]$_x$(SiO$_{4/2}$)$_y$ wherein x and y may, for example, range from 50 to 80. Such siloxysilicates are commercially available from General Electric, Dow Corning, Wacker, Milliken, Siltech, Grant Industries, Momentive and Shin-Etsu Silicones under the tradename Resin MQ®.

According to preferred embodiments, the long-wear lip compositions contain silsesquioxane resins such as, for example, polypropyl silsesquioxane resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film-forming resin is made up predominantly of tri-functional units (or T units), it is generally called a silsesquioxane resin, which is described, for example in US 2006/0292096, herein incorporated by reference in its entirety.

Examples of silsesquioxane resins that may be used in the present invention are alkyl silsesquioxane resins that are silsesquioxane homopolymers and/or copolymers having an average siloxane unit of the general formula $R^1{}_n SiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer includes $R^1SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference in their entirety.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of $RnSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer includes $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

According to preferred embodiments, the long-wear lip composition contains at least one silicone resin selected from the group consisting of siloxysilicate resins, silsesquioxane resins, and mixtures thereof.

The at least one silicone resin is preferably present in the compositions of the present invention in an amount ranging from about 0.5%, 1%, or 1.5% to about 1.5%, 2%, 4%, 6% or 10% by weight, all weights being based on the weight of the composition as a whole.

Silica Aerogel

Compositions of the present invention include a silica aerogel. The "silica aerogel" according to the present invention is a porous material obtained by replacing (by drying) the liquid component of a silica gel with air. Silica aerogels are generally synthesized via a sol-gel process in a liquid medium and then dried, usually by extraction with a supercritical fluid, such as, but not limited to, supercritical carbon dioxide ($CO_2$). This type of drying makes it possible to avoid shrinkage of the pores and of the material.

The silica aerogel (e.g., hydrophobic silica aerogel particles) used in the present invention have a specific surface area per unit of mass ($S_M$) ranging from about 500 to about 1500 $m^2/g$, or alternatively from about 600 to about 1200 $m^2/g$, or alternatively from about 600 to about 800 $m^2/g$, and a size expressed as the mean volume diameter (D[0.5]), ranging from about 1 to about 30 μm, or alternatively from about 5 to about 25 μm, or alternatively from about 5 to about 20 μm, or alternatively from about 5 to about 15 μm. The specific surface area per unit of mass may be determined via the BET (Brunauer-Emmett-Teller) nitrogen absorption method. The BET specific surface area corresponds to the total specific surface area of the particles under consideration.

The size of the particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. The particles used in the present invention may advantageously have a tamped (or tapped) density ranging from about 0.04 $g/cm^3$ to about 0.10 $g/cm^3$, or alternatively from about 0.05 $g/cm^3$ to about 0.08 $g/cm^3$. In the context of the present invention, this density, known as the tamped density, may be assessed according to the following protocol: 40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica aerogel particles used in the present invention have a specific surface area per unit of volume $S_V$ ranging from about 5 to about 60 $m^2/cm^3$, or alternatively from about 10 to about 50 $m^2/cm^3$, or alternatively from about 15 to about 40 $m^2/cm^3$. The specific surface area per unit of volume is given by the relationship: $S_V=S_M·r$ where r is the tamped density expressed in $g/cm^3$ and $S_M$ is the specific surface area per unit of mass expressed in $m^2/g$, as defined above.

In some embodiments, the silica aerogel particles, according to the invention, have an oil-absorbing capacity, measured at the wet point, ranging from about 5 to about 18 ml/g, or alternatively from about 6 to about 15 ml/g, or alternatively from about 8 to about 12 ml/g. The oil-absorbing capacity measured at the wet point, noted Wp, corresponds to the amount of water that needs to be added to 100 g of particle in order to obtain a homogeneous paste. Wp is measured according to the wet point method or the method for determining the oil uptake of a powder described in standard NF T 30-022. Wp corresponds to the amount of oil adsorbed onto the available surface of the powder and/or absorbed by the powder by measuring the wet point, described below: An amount=2 g of powder is placed on a glass plate, and the oil (isononyl isonanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted. The oil uptake corresponds to the ratio Vs/m.

The aerogels used, according to the present invention, are hydrophobic silica aerogels, preferably of silylated silica (INCI name: silica silylate). The term "hydrophobic silica" means any silica whose surface is treated with silylating agents refers to any silica whose surface is treated with silylating agents, for example, halogenated silanes, such as alkylchlorosilanes, siloxanes, in particular dimethylsiloxanes, such as hexamethyldisiloxane, or silazanes, so as to functionalize the OH groups with silyl groups Si—Rn, for example, trimethylsilyl groups. Preparation of hydrophobic silica aerogel particles that have been surface-modified by silylation, is found in U.S. Pat. No. 7,470,725, incorporated herein by reference. In one embodiment, hydrophobic silica aerogel particles surface-modified with trimethylsilyl groups are desirable.

Suitable examples of hydrophobic silica aerogels, may include, but are not limited to, the aerogels sold under the tradenames of VM-2260 (INCI name: Silica silylate) and VM-2270 (INCI name: Silica silylate), both available from Dow Corning Corporation (Midland, Mich.). The particles of VM-2260 have a mean size of about 1000 microns and a specific surface area per unit of mass ranging from 600 to 800 m$^2$/g. The particles of VM-2270 have a mean size ranging from 5 to 15 microns and a specific surface area per unit of mass ranging from 600 to 800 m$^2$/g. Another suitable example of a hydrophobic silica aerogel may include, but is not limited to, the aerogels commercially available from Cabot Corporation (Billerica, Mass.) under the tradename of Aerogel TLD 201, Aerogel OGD 201 and Aerogel TLD 203, Enova Aerogel MT 1100 and Enova Aerogel MT 1200.

The silica aerogel is in certain embodiments a hydrophobic silica aerogel, such as silica silylate.

The silica aerogel is present in compositions of the invention in a concentration by weight of at least about 0.1%, such as from about 0.10, 0.25, or 0.50, to about 0.5%, 0.75%, 1%, 2%, 3% or 5%.

Spherical Silica

Compositions of the present invention include a spherical silica. By "spherical silica," it is meant a particulate silica that is substantially spherical. In certain embodiments, the spherical silica is a "native" silica, i.e., free of hydrophobic surface treatments and may be at least 90%, such as at least 95% such at least 98% chemical purity with respect to silica. The spherical silica may be a spherical amorphous silica. According to certain embodiments, the mean size of these particles of spherical amorphous silica is less than 15.0 microns and more particularly ranges from 3 to 10 microns.

The particles of spherical amorphous silica useful according to the invention are colorless or white solid particles of any form, which are in a form that is insoluble and dispersed in the medium of the composition.

Suitable examples include porous silica microspheres sold under the name SilicaBeads SB-700 by the company Myoshi (mean size 4.6 microns and oil absorption capacity Wp: 133 ml/100 g); Sunsphere® H51 (mean size 5.1 microns and oil absorption capacity Wp: 133 ml/100 g), Sunsphere® H33 (mean size 2.9 microns and oil absorption capacity Wp: 370 ml/100 g) by the company Asahi Glass.

The concentration by weight of the spherical silica in the composition may range from about 1%, 1.5%, or 2.0% to about 3.5%, 5%, 7%, or 10% by weight.

Clay

Compositions of the present invention include a clay. According to certain embodiments, the clay has a low swelling capacity. An example of such as clay is kaolin. One suitable kaolin is SUPREME™ Kaolin available from Imerys, which has an average particle size of about 0.4 microns. In certain embodiments, the kaolin is uncoated.

The inventors have found that the clay serves to provide mattity and, if used in relatively low concentrations will not adversely create "drag" in applying the product to the skin. The concentration of the clay in the composition may range from about 0.5%, 0.75% or 1% to about 1.5%, 2%, 3%, 5% or 6% by weight.

Additionally, swellable clays may also be included. An example of a swellable clay are smectite clays. The crystal structure of the smectite group, is an octahedral alumina sheet between two tetrahedral silica sheets. In one notable embodiment, the swellable clay is bentonite. Bentonite is a rock formed of highly colloidal and plastic clays composed mainly of montmorillonite, a clay mineral of the smectite group, and is produced by in situ devitrification of volcanic ash. In addition to montmorillonite, bentonite may contain feldspar, cristobalite, and crystalline quartz. Bentonite has an ability to form thixotrophic gels with water, an ability to absorb large quantities of water. Variations in interstitial water and exchangeable cations in the interlayer space affect the properties of bentonite and thus the commercial uses of the different types of bentonite.

One notable swellable clay suitable for use in the composition is BENTONE 38VCG, commercially available from Elementis Specialties, East Windsor, N.J. BENTONE 38VCG is disterdimonium hectorite. The swellable clay may be present in concentrations ranging from about 0.5%, 1% or 2% to about 2%, 3% or 5%.

Starch

Compositions of the present invention include a starch. Starches suitable for use in the present invention include those derived from rice, corn, or tapioca. In one notable embodiment, the starch is derived from corn. The starch may be modified, such as with a hydrophobic compound or unmodified ("native").

Suitable modified starches include hydrophobically modified starches such as those modified with octenylsuccinic anhydride-esterified starch salts. Among the octenylsuccinic anhydride-esterified starch salts that may be used include salts of calcium, sodium or aluminum salts obtained by reacting octenylsuccinic anhydride with a maize starch, and in particular the following esterified maize starch salts designated below under their INCI name: aluminum starch octenylsuccinate sold especially under the trademark "Dry Flo Plus" or "Dry Flo Pure" by National Starch; sodium starch octenylsuccinate sold especially under the trademark "Capsul" by National Starch; and calcium starch octenylsuccinate sold under the trademark "Skin Flow-C" by Midwest Grain Products. Aluminum starch octenylsuccinate is particularly notable.

In certain other embodiments, the starch is a native starch such as *Zea Mays* corn starch available from Roquette (Sante Fe Springs, Calif.)

The starch may be selected so as to provide some mattity to the composition as applied to the skin and also so as to create some slip during application.

The concentration of the starch in the composition may range from about 0.5%, 0.75% or 1% to about 1.5%, 2%, 3%, or 5% by weight.

According to certain embodiments, the emulsion composition may meet certain requirements with respect to the clay, the starch, the spherical silica and silica silylate. For example, each of the clay, the starch, the spherical silica and silica silylate may be present in concentrations by weight less than about 6.5%, such as from about 0.25% to about 6.5%, such as from about 0.25% to about 5%.

According to certain other embodiments, the sum of the concentrations by weight of the clay, the starch, the spherical silica and the silica silylate is from about 3% to about 10%, such as from about 3% to about 8%.

The inventors have found that emulsion compositions of the present invention, when the above particulate materials are each present in the concentration ranges above and/or sum to the concentrations above, provide a surprisingly good combination of stability and texture.

Pigment

Compositions of the present invention include a pigment. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles (exclusive of clay, spherical silica, silica silylate and starch). Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of pigment employed in the compositions of the present invention will depend on the color, intensity and use of the cosmetic composition and, as a result, will be determined by those skilled in the art of cosmetic formulation. However, one preferred amount of pigment for use in the present invention is from about 3%, 5%, or 8 to about 10%, 12%, 15% or 20%, based on the weight of the composition. In certain embodiments the pigment includes or is selected from uncoated or coated particulate iron oxide, uncoated or coated titanium dioxide particles, and combinations thereof.

According to certain embodiments, the concentration by weight of the particulate iron oxide the less than each of the concentration by weight of the clay, the concentration by weight of the starch, and the concentration by weight of the spherical silica.

Emulsifier

The compositions of the present invention include one or more emulsifiers suitable to stabilize the emulsion. A wide variety of emulsifiers may be used and, in particular, the emulsifiers will include at least one low HLB emulsifier (HLB less than about 6 or 7).

The emulsifier has having hydrophilic and hydrophobic portions and when present in water in a concentration of 0.5%, may be able to reduce surface tension of water at ambient temperature and pressure to less than about 60 mN/m, such as less than about 50 mN/m.

The emulsifiers may be non-ionic. Useful non-ionic emulsifiers can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; poly-ethoxylated fatty acid mono or diesters of glycerol ($C_6$-$C_{24}$) alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof. In certain embodiments, the emulsifiers include, for example, hydrocarbon esters or silicones that have been rendered surface active such as by reacting with alkoxylates or polyalkylene glycols. Examples include Cetyl PEF/PPG dimethicones; PEG-10 dimethicone; PEG-4 isostearate, and the like.

According to preferred embodiments, the compositions of the present invention contain from about 2%, 3%, 4% or 5% to about 6%, 8%, or 10% by weight of emulsifier.

Water

Compositions of the present invention include water in an internal phase. The concentration of water may be less than about 50%, such as less than about 40%, such as from about 10%, 20% or 30% to about 30%, 40%, or 50%.

Other Components

Various other components may be included in compositions of the present invention. These other components include, for example, solvents such a monoalcohols and glycols; thickening polymers; chelating agents, inorganic or organic sunscreens, preservatives, skin active agents, vitamins, and the like. These other components may be present in concentrations of less than about 20%, such as less than about 10%. In certain embodiments, organic sunscreen is present in a concentration from about 0.5%, 1%, or 2% to about 6%, 10% or 15%. In certain other embodiments, the organic sunscreen is or includes octocrylene.

METHODS OF MAKING AND USING

Compositions of the present invention are prepared by combining the silicone oil, other compounds soluble in the silicone oil, emulsifiers, and pigments having hydrophobic coatings, are mixed to form a fatty phase. The mixture is then subject to a grinding step using a high shear mixer (e.g., Silverson) an optional ice bath. The fatty phase is combined with a separately prepared water phase that includes water and other water-soluble ingredients. This combination is heated and mixed at elevated temperature to form a uniform emulsion having a fatty external phase. Separately, powders such as starch, spherical silica, silica silylate, and clay are blended together and then added into the batch until well dispersed with a homogenizer. Separately, silicone resin and optional hydrocarbon solvents are blended together and then added to the main batch and mixed until uniform.

Methods according to the disclosure comprise making-up, treating, caring for, or conditioning keratin substrates with the compositions described herein. The methods generally comprise applying any of the disclosed makeup compositions to the keratinous substrates, e.g. to the skin. In certain embodiments, the keratinous substrate is the skin of the face including around the neck, cheeks, forehead, eyelids, and the like. In other embodiments, the keratinous substrate is skin around other areas of the body such as legs, arms, and the like.

EXAMPLES

The following examples are intended to be non-limiting and explanatory in nature only. The samples were nearly identical, except that certain concentrations of ingredients were allowed to vary as per the table below. Aside from the ingredients listed below, the samples all had identical or approximately identical concentrations of oils, emulsifier, pigments, water, monoalcohols, glycols, and pigments (coated iron oxide and coated titanium dioxide). All the samples had about 7% by weight of combined concentration of kaolin clay, starch, silica aerogel and spherical silica. In the Examples, amounts are expressed in percentage by weight (wt %) of active materials.

| Reference | Silicone resin | Clay | Starch | Spherical silica | Silica silylate |
|---|---|---|---|---|---|
| Ex. 1 | 1-5% | 1-3% | 0.5-3% (coated) | 3-6.5% | 0.5-1% |
| 2 | 0% | 1-3% | 0.5-3% | 3-6.5% | 0.5-1% |
| 3 | 1-5% | 0% | 0.5-3% | 3-6.5% | 0.5-1% |
| 4 | 1-5% | 1-3% | 0% | 3-6.5% | 0.5-1% |
| 5 | 1-5% | 6.7% | 0.5-3% | 0% | 0% |
| 6 | 1-5% | 7.9% | 0% | 0% | 0% |
| 7 | 1-5% | 0% | 0% | 7.9 | 0% |
| 8 | 1-5% | 0% | 7.9 (native) | 0% | 0% |
| 9 | 1-5% | 0% | 7.7 (coated) | 0% | 0% |

The samples were evaluated for stability at 45 C (holding at temperature for 2 months) as well as for texture on application.

Example 1 was stable at 45 C and had a pleasant texture, neither draggy nor slippery on the skin.

Example 2, with no silicone resin, was unstable at 45 C (slight layer of oil on top).

Example 3, with no kaolin, was unstable at 45 C (slight layer of oil on top).

Example 4, with no starch, was unstable at 45 C (slight layer of oil on top) and when applied to the face provided insufficient mattity.

Example 5, with kaolin and no spherical silica and no silica silylate showed a separation of the fatty phase and had a draggy feel when applied to the skin.

Example 6, with kaolin and no spherical silica, no silica silylate and no starch was unstable at 45 C and was also draggy and had an ashy appearance on the skin.

Example 7, with spherical silica and no kaolin, no silica silylate and no starch was unstable at 45 C and was very slippery on the skin.

Example 8, with starch (native) and no spherical silica, no silica silylate and no kaolin was unstable at 45 C and was draggy on the skin.

Example 9, with starch (hydrophobically coated) and no spherical silica, no silica silylate and no kaolin was unstable at 45 C and was draggy on the skin.

The invention claimed is:

1. A make-up emulsion composition, comprising:
an aqueous internal phase emulsified in an external fatty phase, wherein the fatty phase comprises at least one silicone oil;
from 1% to 5% by weight of silicone resin;
from 0.5% to 1% by weight of silica silylate;
from 3% to 6.5% by weight of spherical silica;
from 1% to 3% by weight of clay;
from 0.5% to 3% by weight of starch;
pigment;
emulsifier, and
optionally monoalcohol which, if present, is present in an amount of less than about 10% by weight,
all weights being with respect to the weight of the composition, wherein:
(i) the clay is kaolin;
(ii) the silicone resin is trimethylsiloxysilicate; and
(iii) the starch is Zea Mays corn starch and/or octenylsuccinic anhydride-esterified starch salt(s).

2. The composition of claim 1, wherein the sum of the concentrations by weight of the clay, the starch, the spherical silica and the silica silylate is from 5% to about 10%.

3. The composition of claim 1, wherein the sum of the concentrations by weight of the clay, the starch, the spherical silica and the silica silylate is from 5% to about 8%.

4. The composition of claim 1, wherein the pigment comprises particulate iron oxide, particulate titanium dioxide or combinations thereof.

5. The composition of claim 1 wherein the clay is uncoated kaolin.

6. The composition of claim 1, wherein the at least one silicone oil is dimethicone.

7. The composition of claim 1, wherein the composition further comprises a smectite clay.

8. A method of making-up the skin, comprising applying an emulsion composition, to the skin, wherein the emulsion composition comprises:
an aqueous internal phase emulsified in an external fatty phase, wherein the fatty phase comprises at least one silicone oil;
from 1% to 5% by weight of silicone resin;
from 0.5% to 1% by weight of silica silylate;
from 3% to 6.5% by weight of spherical silica;
from 1% to 3% by weight of clay;
from 0.5% to 3% by weight of starch;
pigment;
emulsifier, and
optionally monoalcohol which, if present, is present in an amount of less than about 10% by weight,
all weights being with respect to the weight of the composition, wherein:
(iv) the clay is kaolin;
(v) the silicone resin is trimethylsiloxysilicate; and
(vi) the starch is Zea Mays corn starch and/or octenylsuccinic anhydride-esterified starch salt(s).

9. The method of claim 8, wherein the sum of the concentrations by weight of the clay, the starch, the spherical silica and the silica silylate is from 5% to about 10%.

10. The method of claim 8, wherein the sum of the concentrations by weight of the clay, the starch, the spherical silica and the silica silylate is from 5% to about 8%.

11. The method of claim 8, wherein the pigment comprises particulate iron oxide, particulate titanium dioxide or combinations thereof.

12. The method of claim 8 wherein the clay is uncoated kaolin.

13. The method of claim 8, wherein the at least one silicone oil is dimethicone.

14. The method of claim 8, wherein the composition further comprises a smectite clay.

\* \* \* \* \*